United States Patent [19]

Exner

[11] Patent Number: 5,904,925
[45] Date of Patent: May 18, 1999

[54] ADJUVANT FOR ANTIGENS, AND PROCESS FOR MAKING

[76] Inventor: Heinrich Exner, Birkenweg 29, 39291 Möckern, Germany

[21] Appl. No.: 08/656,193

[22] PCT Filed: Dec. 7, 1994

[86] PCT No.: PCT/DE94/01495

§ 371 Date: Dec. 9, 1996

§ 102(e) Date: Dec. 9, 1996

[87] PCT Pub. No.: WO95/15768

PCT Pub. Date: Jun. 15, 1995

[30] Foreign Application Priority Data

Dec. 9, 1993 [DE] Germany ............................. 43 41 938
Dec. 5, 1994 [DE] Germany ............................. 44 45 074

[51] Int. Cl.⁶ ..................... A61K 45/00; A61K 39/085; A61K 39/295
[52] U.S. Cl. ..................... 424/282.1; 424/278.1; 424/243.1; 424/201.1
[58] Field of Search ........................... 424/184.1, 197.11, 424/78.17, 243.1, 282.1, 201.1, 278.1

[56] References Cited

U.S. PATENT DOCUMENTS

| 3,577,524 | 5/1971 | Pratt ........................................ 424/89 |
| 4,297,272 | 10/1981 | d'Hinterland et al. .................. 260/112 |
| 4,397,838 | 8/1983 | d'Hinterland et al. .................... 424/92 |
| 5,571,531 | 11/1996 | McDermott et al. . |

FOREIGN PATENT DOCUMENTS

| 13851 | 8/1980 | European Pat. Off. . |
| 1369334 | 1/1968 | France . |
| 2446111 | 8/1980 | France . |
| 265992 | 3/1989 | Germany . |

OTHER PUBLICATIONS

Bonfield, TL. et al. J. Biomedical Mat. Res. 26:837–850, 1992.
Bartfeld, H. et al. Ann N.Y. Acad. Sci. 243 : 81–90, 1975.
Nisluihata, T. et al. J. Pharm. Pharmacol 37:159–63, 1985.
Hentrich, B. et al. Int. J. Parasitol. 23(6):771–6, 1993.
Vacheron, F. et al. Infect. Immunity 42(3):1049–54, 1983.

*Primary Examiner*—Paula K. Hutzell
*Assistant Examiner*—Lin Sun-Hoffman
*Attorney, Agent, or Firm*—Schweitzer Cornman Gross & Bondell LLP

[57] ABSTRACT

Adjuvants are disclosed for antigens such as viruses, bacteria and parasites, including their metabolic products or parts of the virus, bacteria and parasite structures for the immunization, as well as a process for producing such adjuvants and their uses. The object of the invention is to create adjuvants that in combination with vaccine antigens or with peptidoglycanes in histocompatible composition allow the defence mechanisms in the body to be stimulated to such a large extend that for the first time besides active immunoprophylaxis a even of weak antigens also a general and specific immunotherapy is made possible. The cost of producing the adjuvant should not exceed the usual cost and should ensure the applicability of the vaccine. In relatively weak immuno-incompetent phases of life, a combination of general immunoprophylaxis or the only use of the adjuvant should ensure a high immuno-competence. Residual effects of the adjuvant should not cause any problems. The disclosed adjuvants are oil-in-water emulsions. The oil phase consists of polydimethyl siloxanes and the aqueous phase substantially consists of a biocompatible salt solution. The oil phase is stabilised in the water phase by means of a complex emulsifying agent with HLB value from 9 to 16. The complex emulsifying agent is a combination of aliphatic alcohols of sorbitol with 10 to 100 carbon atoms in the chain and/or of glycerol fatty acid esters and polysorbates. The biocompatible salt solution is a phosphate-buffered sodium chloride solution with EDTA sodium. The combination further contains dimethylsulfoxide. A complete adjuvant is produced by adding peptidoglycanes based on species-specific St. Aureus strains and water-soluble natural and/or synthetic polymers.

20 Claims, No Drawings

ADJUVANT FOR ANTIGENS, AND PROCESS FOR MAKING

FIELD OF THE INVENTION

The present invention relates to adjuvants or enhancers for antigens, such as viruses, bacteria and parasites, including their metabolic products or parts of the structures of viruses, bacteria and parasites for immunization, and a process for producing.

BACKGROUND

Vaccines are administered to improve the development of antibodies with the help of adjuvants. Adjuvants are to retard the absorption of parenterally administered antigens and contribute to a long antigen stimulus. Thus, adjuvants act as enhancers of the immunogenic effect of antigens.

A well known adjuvant is the Freund adjuvant. In its intermediate form, it is a mineral oil-in-water emulsion which can provoke a substantial response from the immune system, while the finished form is produced by the addition of inactivated mycobacteria to the intermediate for considerably higher immunostimulation. The adjuvant action of inactivated mycobacteria is attributed to a growth fraction contained therein. The finished Freund adjuvant frequently causes granuloma formation at the site of the application. The original, finished Freund adjuvant is therefore used only for experimental purposes involving animals.

Aluminum compounds, in the form of hydroxides or phosphates, are frequently used in medicine as adjuvants. Through coupling with vaccine antigens, the so-called adsorbate, these aluminum compounds result in vaccines, the immunopotentiation action of which is explained by the resulting vaccine depots, from which the release of antigen for adsorption is retarded. The aggregation and settling tendencies of solid aluminum compounds, as well as the behavior of their residue, is a disadvantage of the use of these compounds.

A stable water-in-oil emulsion is a further development of an intermediate Freund adjuvant, which, as is well known, includes a mineral oil, a simple emulsifier such as mannitol monooleate, physiological salt solution and Tween 80. These components usually are dispersed with a strong homogenizer, and finished with specific vaccine antigens into the vaccine.

It is a common feature of all of these vaccines, which are based on the oil-in-water emulsion, that the antigen is dispersed only in the aqueous phase of the emulsion. Consequently, a correspondingly long depot action of the antigen is not achieved. Since the viscosity of water-in-oil emulsions is relatively high, it is difficult to administer them. Therefore, hypodermic needles with a large diameter must be used. Moreover, all generally used equipment requires intensive cleaning because of the oiling.

Granuloma may be formed at the site of the injection, as a result of which the antigens are rapidly incorporated over the lymph tracts.

According to the literature, the stability at 37° C. does not exceed one week. After that, there is phase separation and the emulsion is destroyed.

It is also a disadvantage that high-power homogenizers are absolutely essential for producing these water-in-oil emulsions. It is furthermore, disadvantageous that the emulsion must be transported and kept refrigerated.

In the East German patent No. 265 992, an adjuvant is described for immunization as well as methods for producing the same. The oil-in-water emulsion that is used, results in a vaccine having a low viscosity, and requires no special technique of administration. The apparatus can be cleaned without extra expense and the use of the suggested dipolar aprotic solvent guarantees the dispersal of the antigen in the aqueous and oil phases thus, increasing the immunizing effect. Relatively little mechanical energy is required for producing the oil-in-water emulsion, so that simple stirring is sufficient for producing an emulsion of this type. The oil portion of the emulsion is a mineral oil and can optionally contain silicone oils.

It is a disadvantage of this adjuvant that the use of mineral oils, in this case paraffin oils, is associated with a series of problems with regard to the stability of the oil-in-water emulsion. For example, the viscosity of the mineral oil can be varied only within narrow limits. This causes relatively large particles to be formed during the dispersal of the oil droplets. Larger oil droplets cause an increase in the overall viscosity of the emulsion and the associated disadvantages and also unfavorably affect the stability of the emulsion, because cream formation in the oil cannot be avoided, particularly after the emulsion has been standing for some time. The polydisperse particle size distribution of the oil droplets in this oil-in-water emulsion also leads to unstable relationships and histo-incompatibilities.

A further disadvantage is the residue behavior of the mineral oils, which results in incompatibilities with the organism and, when used in animals, can render the animals unfit for human consumption.

Mineral oils also tend to attack certain antigens and thus make the vaccines ineffective.

The use of dipolar aprotic solvents, such as dimethyl sulfoxide, in conjunction with mineral oils will also not bring about the expected depot effect. Evidently, a slow resupplying of antigens from the oil phase into the aqueous phase (boosting), by the exchange of the antigens between the aqueous phase and the oil phase is not optimally obtained in the presence of a dipolar aprotic solvent.

SUMMARY OF THE INVENTION

It is an object of the invention to provide adjuvants which, through the combination with vaccine antigens as intermediate or incomplete adjuvants, or in combination with peptidoglycans in a histocompatible formulation as finished or complete adjuvants, enable stimulation of the defense mechanism of the body to such an extent that, aside from the active immunoprophylaxis even of weaker antigens, general and specific immunotherapy becomes possible for the first time. At the same time, the adjuvant produced in accordance with the invention should not be uncommonly expensive and should permit the normal administration of the vaccine. A high degree of immunological competence should be achieved even in relatively immunologically incompetent life sections by a combination of the general immunological prophylaxis or by the sole use of the adjuvant. The residual behavior of the adjuvant should not be associated with any problems.

The foregoing objectives are accomplished in accordance with the present invention with adjuvants for antigens, a method for making.

An improved vaccine can be prepared with the intermediate adjuvant of the present invention, and for antigens such as viruses, bacteria and parasites, including their metabolic parts as products. The intermediate adjuvants of the present invention are oil-in-water emulsions and can be used with other vaccines for producing the improved vaccines. Thus the intermediate adjuvant of the present invention improves the properties of the vaccine. The oil phase comprises polydimethysiloxanes and the aqueous phase contains a biocompatible salt solution. The oil phase is stabilized in the aqueous phase by a complex emulsifier, which has an HLB hydrophilic-lipophilic balance value of 9 to 16. The complex emulsifier is suitably a combination of $C_{10}$ to $C_{100}$ aliphatic alcohols, such as sorbitol, and/or esters of glycerol and fatty acids, and of polysorbates. The biocompatible salt solution is a phosphate-buffered sodium chloride solution containing chelating agents. Pursuant to the invention, the combination additionally contains dimethyl sulfoxide distributed between the two phases according to its solubility.

Suitably polyhudric, water-soluble alcohols such as glycerol is added. Addition particularly of chelating agents, results in a further stabilization of the emulsion.

Optimally, the finished adjuvant is suitably prepared in accordance with the invention by the addition to the intermediate adjuvant peptidoglycans, based on species-specific *Staphylococcus aureus* strains and water-soluble natural and/or synthetic polymers to the intermediate adjuvant. The finished adjuvant can be employed along for immunostimulation, or, can be employed for the production of a vaccine with weakened or inactive antigens. The water-soluble polymers, present in the finished adjuvant, exert an additional stabilizing effect on the emulsion. They furthermore have an exceptionally advantageous effect on the release of the antigens at the injection site, as well as from the oil phase and the aqueous phase.

The polydimethylsiloxanes can be varied within wide limits with respect to their viscosity by the appropriate selection of the degree of polymerization.

It was surprisingly observed that a finely divided emulsion with a narrow particle size distribution of the oil droplets can be produced by the combination between polydimethylsiloxane as oil phase and through the use of the complex emulsifier. This enables rapid dispersal the vaccine depot at the injection site in the presence of dimethyl sulfoxide with retention of the booster effect. A high histocompatibility is thus attained, which is a prerequisite for the use of polydimethylsiloxanes.

The interaction of polydimethylsiloxanes with peptidoglycans based on *Staphylococcus aureus* strains leads to a remarkable, previously unknown intensity of the nonspecific immune response of T and B cells.

Pursuant to the present invention, the finished adjuvant for antigens, such as viruses and bacteria, parasites, including the metabolic products and parts of the structure of viruses, bacteria and parasites, is produced for immunization by adding an aqueous composition of peptidoglycans to the glycerol-containing intermediate adjuvant. The aqueous composition contains salt and is based on specific *Staphylococcus aureus* strains, and water-soluble and natural and/or synthetic polymers, species-specific strains of *Staphylococcus aureus*, which are incubated on 5% blood agar for 24 hours, and selected for the preparation of the peptidoglycans. The harvested staphylococci are taken up in 0.5% phosphate-buffered phenol/salt solution and inactivated for 48 hours at 37° C. The inactivated staphylococci are separated, washed and taken up in a 5% solution of an aqueous, natural and/or synthetic polymer in salt solution and autoclaved. The treatment in the autoclave is optimally carried out at 121° C. The dosage of peptidoglycans lies between $10^2$ and $10^9$, based on the harvested organisms, per ml of finished vaccine.

Partially synthetic cellulose esters, polyvinylpyrrolidone and poly-6-aminohexanoic acid as well polyvinylalcohol, alkali and ammonium alginate, methylcellulose, ethylcellulose, hydroxyethylcellulose, ethylhydroxyethylcellulose, and sodium-carboxymethylcellulose have particularly proven their value as water-soluble polymers, which are to be used pursuant to the invention.

The polydimethylsiloxanes, used pursuant to the invention, offer various advantages. For example, they are particularly resistant to oxidative and hydrolytic effects and to the effects of temperature and the viscosity dependence on temperature is slight. Moreover, they are odorless and tasteless. Since the viscosity increases with the degree of polymerization, it is readily possible to adjust the viscosity of the emulsion to the desired value. Moreover, in contrast to a mineral oil, the temperature dependence of a polydimethylsiloxane is very low. For example, a polydimethylsiloxane, with a linear chain structure and a viscosity of 500 cSt, is particularly suitable for producing finely divided and essentially homodisperse emulsions. The relatively low surface tension of polydimethylsiloxanes permits the desired distributions of the oil phase in the aqueous phase to be attained pursuant to the invention by spontaneous emulsification with suitable complex emulsifiers. The complex emulsifiers, used pursuant to the invention for this purpose, are suitably $C_{10}$ to $C_{100}$ aliphatic alcohols, fatty esters of sorbitol, and/or glycerol, and polysorbates. An optimum ratio of the aforementioned three components is suitably 1:1:1.

The hydrophilic-lipophilic balance value referred to hereinafter in the specification and in the claims, as well as in the trade as "HLB") serves to characterize the effect of the complex emulsifiers of the present invention. An HLB value of 12 is advantageous. An optimally-acting complex emulsifier of the present invention includes, for example, polyethoxylated sorbitol hexaoleate, polyethoxylated (20) sorbitol monooleate, and cetyl stearyl alcohol. The peptidoglycans in aqueous solution, are admixed separately for producing the finished adjuvant, or together with the antigen for immunization, to the intermediate adjuvant, suitably at a temperature between 20° to 30° C.

The adjuvants of the present invention function as immunoprophylactics in human and veterinary medicine. They are used for improving the immunoprophylaxis by actively stimulating the cellular and humoral immunocompetence and, due to their mechanism of action, can be used for general and specific immunotherapy. The formulation of the adjuvant brings about a rapid dispersion of the vaccine depot at the injection site, while retaining the booster effect. A high histocompatibility is attained in this manner. The production of the adjuvant does not exceed the usual cost of production and the applicability of the vaccine. Very good temperature stability and stability of the oil-in-water emulsion is assured due to the use of polydimethylsiloxanes. By the combination of an adjuvant of the invention with vaccine antigens alone (as am intermediate adjuvant) or in combination with peptidoglycans in a histologically compatible formulation (as a complete adjuvant), the defense mechanism of the organism is stimulated to such an extent that, aside from the active immunoprophylaxis of weak antigens, general and specific immunotherapy becomes possible for the first time.

The mode of action of the inventive adjuvants also ensures immunostimulation in the case of non-infectious depressions of the immune system, such as prophylaxis and therapy of dystrophic processes, autoimmune diseases, osteopathies, etc.

A high immuno-competence can be achieved in relatively immunoincompetent life sections by a combination with general immuno-prophylaxis or by the sole use of the inventive adjuvant or adjuvants, such as in pediatrics and geriatrics.

EXAMPLE 1

Intermediate Adjuvant 1000 g of intermediate adjuvant is prepared by stirring 5 g of polydimethylsiloxanes, 3.5 g of a complex emulsifier with an HLB value of 12, 2.5 g of glycerol, and 2.1 g of dimethyl sulfoxide, with 986.9 g of biocompatible salt solution which contains 0.2 g of ethylenediaminetetraacetate $Na_2Ca$, and with constant stirring heated to 100° C. and autoclaved at 121° C. and 0.5 atmospheres and subsequently reemulsified by vigorous stirring, commencing at 90° C. and, as the temperature drops further, to below 30° C. The adjuvant produced in this manner can be stored in vials for more than four years at 4° C.

EXAMPLE 2

Finished Adjuvant

The finished adjuvant is prepared by adding the peptidoglycans at a temperature ranging from 20° to 30° C. as an aqueous solution to the intermediate adjuvant prepared according to Example 1. The peptidoglycan concentration per vaccine dose depends on the species specificity, varying from 0.001 to 50 µg of protein nitrogen. The adjuvant can take up an aqueous antigen solution in producing a vaccine therewith.

The peptidoglycan is prepared from species-specific strains of *Staphylococcus aureus* and incubated for 24 hours on 5% blood agar. The harvested staphylococci are taken up in phenol/salt solution, buffered with 0.5% phosphate, and inactivated for 48 hours at 37° C. The inactivated staphylococci are separated, washed and taken up in a 5% poly(2-oxo-1-pyrrolidinyl) ethylene salt solution and autoclaved at 121° C. The peptidoglycans are then centrifuged off and taken up in a phosphate-buffered salt solution and adjusted to a nitrogen content of 0.001–50 µg per ID. When streptococci are selected as the strains of staphylococci, those strains of the respective species should be selected, which originate from pathogenic processes and, if possible, are hospital strains of the respective type. The complete adjuvant is filled into vaccine bottles depending on the use.

EXAMPLE 3

Pigeons with paramyxo virus infection

A stock of 300 pigeons had contracted a PMV infection. Within 4 weeks, 120 birds had died. At the time of the vaccination, 40 of the 180 remaining birds were clinically severely ill and the remaining 140 were morbid.

All birds were vaccinated with 1 ml of intermediate adjuvant of Example 1 used with $10^6$ EID of PMV antigens per ml. 25% more of the 40 severely ill birds died from the remaining 3% of the birds.
Result:

Already after 3 to 5 days, the state of health had stabilized appreciably. The dying abated and even birds with an extremely altered general state of health returned to normal.
Epicrisis:

The pigeons were immunized with a water-in-oil adjuvant PM vaccine three weeks before the immunization with the intermediate adjuvant without any other effect (no vaccine chicken against paramyxo virus) than for paramyxis. It became clear for the first time that it was possible to vaccinate into an infection with the intermediate adjuvant and PMV antigen and to improve the clinical picture suddenly within 3 to 5 days after administration.

EXAMPLE 4

Pigeons with Salmonellosis

S.t.m. infection existed in a stock of about 50 birds over several years. Treatment with antibiotics according to antibiogram produced no permanent results. Even inactivated S.t.m. was unable to control the process.

The total stock of birds was immunized with the intermediate adjuvant of Example 1 using 1 ml per bird and $10^9$ inactivated S.t.m. organisms per ml resulting in optimum protection. A booster 4 weeks after the first vaccination brought about an improvement in the raising of young pigeons and the bradycation of the S.t.m. infection. Nestlings were included with good compatibility in the immunization with intermediate adjuvant.

EXAMPLE 5

Chicken with slow virus infection - broiler grandparent reproduction breed

Since the middle of the 1980's, an increase in the so-called malabsorption syndrome (a slow virus infection) also known as helicopter disease, brittle bone disease, standing syndrome, femoral head necrosis, leg problems, etc. has been described in Europe and throughout the world. In association with this, opportunistic infections, such as Marek's disease, coccidiosis, *Staphylococcus aureus* arthritis, salmonella, etc. have occurred.

Clinically, there is already an appreciable growth difference at the age of 2 to 4 weeks in these flocks having the standing syndrome. By the time the chickens are ready to lay eggs at the age of 20 to 24 weeks, up to about one-quarter of the flock can be lost. In a flock of about 7000 birds, up to 10% to 15% of the birds are underweight already at the age of 3 weeks. The weights of the underweight chicken were of the order of 65% of the weight of the average of the group. The affected birds grow considerably slower; have poor feather development and increased susceptibility to disease. These chickens can constitute up to 25% of the young breed. As a result of the increased susceptibility to disease, opportunistic infectious diseases, which frequently are difficult to control, occur in these flocks even after the start of laying. By experimental vaccination with a finished adjuvant of Example 2, it was observed that the flock recovered and the emaciated chicken were able to regain a large portion of their weight within 10 to 14 days through free feeding; the morbidity of opportunistic diseases also decreased. This effect did not occur when conventional, commercial oil-emulsion vaccines were used for comparison.

After these observations, further flocks were immunized as follows with the finished adjuvants using a vaccination 1 ml dose of finished adjuvant (with ND (Newcastle Disease), IB (avian infectious bronchitis) and IBD (infectious bursal disease) per vaccination dose). The serology corresponding to titers of comparable oil emulsion adjuvants. According to the growth curves, the first immunization was carried out immediately before the first occurrence of the standing syndrome at the age of 3 to 4 weeks, the second at the age of 10 to 12 weeks and the third at the age of 18 to 20 weeks with a finished adjuvant. After this immunization program, the growth curves once again became linear and the losses decreased to the normal rate. The effects were particularly clear in the case of MK and leukosis. Without changes in the MK vaccination program, the losses due to the formation of neoplasms decreased to the extent that they approached zero.

Epicrisis:

The standing syndrome was cured by vaccination with a finished adjuvant and all other problems of opportunistic diseases were repressed to a minimum. No such effects were achieved by vaccinations carried out for comparison with mineral oil-containing vaccines and other flocks. A considerable performance increase in the adult chicken was observed as a result of stabilizing the health in the breed.

A limited generation effect could be detected after the immunization in the individual breeding stages. This effect lasted for 4 weeks and could not be interpreted on the basis of maternal antibodies, that is, these early growth problems of standing syndrome were not observed in the subsequent generation. These effects are being reproduced at the present time in other lines with similar symptoms on approximately 30,000 chickens.

EXAMPLE 6

Furunculosis

Patient had multiple boils on the trunk after delivery. Bacteriological examination revealed *Staphylococcus aureus* with multiple antibiotic drug resistance. Type differentiation revealed strain agreement with hospital staphylococcus organisms in the maternity ward. Conventional therapy failed. An autovaccine with inactivated *Staphylococcus aureus* prevented renewed exacerbation for 4 weeks at most.

Inactivated organisms of the hospital strain of *Staphylococcus aureus* ($10^9$) were transferred into 1 ml of the finished adjuvant of Example 2. Immunization was carried out with 1 ml of the finished adjuvant. The boils commenced to dry out after only 3 days and were healed after 10 days. A further family member of this patient developed boils and was immunized with the finished adjuvant and inactivated *Staphylococcus aureus* with the same effect.

EXAMPLE 7

Staphylococcus infection after a syringe abscess

A patient was desensitized with the specific allergens. After one of these injections, a syringe abscess developed in the buttocks. Despite surgical intervention, the abscess broke through into the minor pelvis. Staphylococci isolated from the blood. Since the general condition deteriorated daily, a finished adjuvant of Example 2 was used as ultimo ratio.

A finished adjuvant of 1 ml with an inactivated *Staphylococcus aureus* at a concentration of $10^9$ organism per ml was intramuscularly administered. The critical condition continued for a further 2 days with a decreasing crisis. The patient arose for the first time after 3 days and was cured after a further 7 days.

EXAMPLE 8

Acne vulgaris

A patient had highly disfiguring acne boils in the face, on the back and on the chest, predominantly in the sweat grooves since the onset of puberty at the age of about 10. Bacteriological examination revealed *Streptococcus pyogenes* and *croynebac-terium acne* with good antibiotic sensitivity. However, since all previous treatments, including an antibiotic treatment, had not brought any improvement, the patient was experimentally vaccinated.

A finished adjuvant of Example 2 without additional antigens was administered. The lower acne boils commenced to heal already after 1 week. After 3 weeks, the vaccination was repeated with the same dose. Six weeks after the first immunization, since even the scars turned pale and no new acne boils developed, the patient developed a completely new facial expression.

EXAMPLE 9

Osteoporosis

A patient with osteoporosis and onset of menopause before the age of 50 was admitted for 4 weeks to an orthopedic clinic for treatment to stabilize the locomotor system. The patient was able to carry out household work only with great effort or outside help. Vaccination was attempted since there was no improvement in this condition even after the hospital stay.

At intervals of 3 weeks, in each case 1 ml of finished adjuvant of Example 2 without further antigen was intramuscularly administered. Two weeks after the second injection, the condition improved so that work in the house became easier once again. After the third vaccination, bone pain abated almost totally and mobility was practically completely restored.

The normal menstruation commenced once again three months after the start of the treatment and no complications occurred during a year of further observation.

I claim:

1. An adjuvant which comprises from 0.01% to 30% of a polydimethylsiloxane, from 0.01% to 15% of a complex emulsifier with an HLB of 9–16, from 45% to 99% of a biocompatible salt solution, from 0.01% to 10% of dimethylsulfoxide, and 0.0001% to 1% of a chelating agent.

2. The adjuvant of claim 1, wherein said polymethylsiloxane has a degree of polymerization of from 20 to 400, and a kinematic viscosity of from 20 to 1000 cst.

3. The adjuvant of claim 1, wherein said complex emulsifier is at least one of a (i) $C_{10}$ to $C_{100}$ aliphatic alcohol, (ii) a fatty acid ester of sorbitol, (iii) glycerol, and (iv) a polysorbate.

4. The adjuvant of claim 3, wherein the ratio by weight of said aliphatic alcohol to fatty acid ester of sorbitol and/or of glycerol to polysorbate is 0.5–3 to 0.2–4 to 1–5.

5. The adjuvant of claim 1, wherein said chelating agent is ethylenediaminetetraacetic acid.

6. The adjuvant of claim 1, further comprising from 0.01% to 10% of a polyhydric, water-soluble alcohol.

7. The adjuvant of claim 6, wherein said polyhydric, water-soluble alcohol is glycerol.

8. A complete adjuvant for antigens, which comprises the adjuvant of claim 1, together with a species-specific bacterial peptidoglycan at a concentration of from 0.00001 to 1 mg of protein nitrogen per mg of adjuvant.

9. The finished adjuvant of claim 8, wherein said bacterial strain is a species-specific strain of *Staphylococcus aureus*.

10. The complete adjuvant of claim 8, further comprising at lest one of a natural and synthetic, water soluble polymer.

11. The complete adjuvant of claim 10 wherein said water-soluble polymer is present at a concentration of 0.0001 to 10 mg per ml of the complete adjuvant.

12. The complete adjuvant of claim 10, wherein said water-soluble polymer is at least one of polyvinylpyrrolidone, poly-6-aminohexanoic acid, polyvinyl alcohol, alkali and ammonium alginate, cellulose, and partially synthetic cellulose ester.

13. The complete adjuvant of claim 8, further comprising from 0.01% to 10% of a polyhydric, water-soluble alcohol.

14. The complete adjuvant of claim 13, wherein said polyhydric, water-soluble alcohol is glycerol.

15. A method for preparing a complete adjuvant for antigens, which comprises adding a salt-containing aqueous composition of a species-specific bacterial peptidoglycan, based on a bacterial strain to the adjuvant of claim 1, incubating said strain on blood agar, harvesting the incubated strain, taking up the harvested strain in a buffered phenol/salt solution, inactivating the taken up strain separating and washing the inactivated strain, taking up said separated and washed strain in a salt-containing aqueous solution of a water-soluble, natural and/or synthetic polymer, and autoclaving the taken up strain at a temperature of more than 121° C.

16. The method of claim 15, further comprising adding to said adjuvant a water-soluble, natural and/or synthetic polymer.

17. The process of claim 15, further comprising converting the product of the process into a vaccine.

18. A process for immunizing an animal host by administering to said host the vaccine of claim 17.

19. The process of claim 15, wherein said species specific strain is a species specific strain of *Staphylococcus aureus*.

20. An immunization process which comprises administering the agent of claim 1 to a host in need therefor.

* * * * *